United States Patent [19]

Schuerer et al.

[11] Patent Number: 4,548,083
[45] Date of Patent: Oct. 22, 1985

[54] CRYOGENIC INSULATION STRENGTH AND BOND TESTER

[75] Inventors: Paul H. Schuerer; James H. Ehl; Willibald P. Prasthofer, all of Huntsville, Ala.

[73] Assignee: The United States of America as represented by the Administrator of the National Aeronautics and Space Administration, Washington, D.C.

[21] Appl. No.: 548,582

[22] Filed: Nov. 3, 1983

[51] Int. Cl.⁴ ............................................. G01N 3/08
[52] U.S. Cl. ................................... 73/827; 73/150 A
[58] Field of Search ................ 73/827, 834, 831, 838, 73/862.38, 862.52, 862.53, 862.54, 826, 835, 150 A; 254/231, 234, DIG. 2; 318/139

[56] References Cited

U.S. PATENT DOCUMENTS

3,464,261 9/1969 Helms .................................... 73/835
3,821,892 7/1974 Saberg .................................... 73/827

Primary Examiner—Jerry W. Myracle
Attorney, Agent, or Firm—Joseph H. Beumer; John R. Manning; Leon D. Wofford, Jr.

[57] ABSTRACT

A method and apparatus for testing the tensile strength and bonding strength of sprayed-on foam insulation (12) attached to metal cryogenic fuel tanks (14). A circular cutter is used to cut the insulation (12) down to the surface of the metal tank to form plugs of the insulation (12) for testing "in situ" on the tank (14). The apparatus comprises an electro-mechanical pulling device (32) powered by a belt battery pack (34). The pulling device (32) comprises a motor (60) driving a mechanical pulling structure comprising a horizontal shaft (64) connected to two bell cranks (68) which are connected to a central member (74). When the lower end of member (74) is attached to fitting (20), which in turn is bonded to plug (10) (see FIG. 2), a pulling force is exerted on plug (10) sufficient to rupture it. The force necessary to rupture the plug (10) or pull it loose is displayed as a digital read-out (51) on screen (50).

15 Claims, 9 Drawing Figures

CRYOGENIC INSULATION STRENGTH AND BOND TESTER

ORIGIN OF THE INVENTION

The invention described herein was made by employees of the U.S. Government and may be manufactured and used by or for the Government of the U.S. of America for governmental purposes without the payment of any royalties thereon or therefor.

TECHNICAL FIELD

The present invention relates generally to testing of insulation on cryogenic containers and more particularly to testing the strength and bonding of foam insulation sprayed on metal cryogenic fuel tanks.

BACKGROUND OF THE INVENTION

Since the advent of the space age which began after the World War II era, the use of liquid fuel rocket engines has become commonplace. These engines often use cryogenic fuels, such as liquid oxygen and liquid hydrogen. Because of the very low temperatures of these fuels in the liquid state, insulated fuel tanks were needed. The application of sprayed-on foam insulation (SOFI) has proved to be the cheapest and best way to put the required insulation on the tanks. Sometimes, however, this foam insulation does not adhere well to the metal fuel tanks. Therefore, these debonded areas must be detected and repaired so that they will not cause problems connected with the firing and use of the high altitude rockets.

A second potential problem is possible weak spots in the sprayed-on foam insulation. This foam, which is a known type of polyurethane foam, is mixed as it is sprayed on. Sometimes, if the mixture is not proper, a reduction in the structural strength of the SOFI is experienced.

At the present time, there is a requirement for a test system to evaluate both the bonding and the strength of the insulation on the external tank of the Space Shuttle (or Space Transportation System, as it is known officially). The external tank (ET) is a tank which is attached to the Space Shuttle to furnish both liquid hydrogen and liquid oxygen to the main engines during launch. The external tank (ET) is completely covered with sprayed-on foam insulation. In addition, in the areas where the greatest amount of heat may develop during flight, such as the front end and the rear dome of the tank, a thin layer of an additional insulation called Super Light Ablator (SLA) is bonded to the tank. In these areas, SOFI is sprayed over the SLA insulation instead of directly on the surface of the ET.

In the recent past a test system called a "Porta Pull" has been used to perform a tensile test on the SOFI of the ET. This test consisted of pulling on a test plug cut in the insulation with an aluminum fitting bonded to the top of the test plug with an adhesive. "Porta Pull" consists of an air cylinder with a base supported on the insulation adjacent to the plug. Force readings are determined by the use of an air pressure regulator and pressure guage. The air cylinder area and the air pressure are used to calculate the tensile force applied to the plug. All testing is performed to failure, and when failure occurs the air cylinder "bounces" off the insulation surface. The "Porta Pull" system is cumbersome and requires the operator to perform calculations. Also the results are not to the desired accuracy.

Perhaps the closest prior art patent known to the applicant is U.S. Pat. No. 3,036,459 to KENDALL. The Kendall patent discloses a method of testing the strength of a reconstituted sponge. A helical spring is screwed into the surface of the sponge to the full length of the spring. A spring scale is then attached to the end of the spring and force is applied along the center line of the long axis of the spring to pull it directly out of the sponge. The force necessary to rupture the sponge and pull out the spring is read on the scale.

Several other prior art devices all have to do with testing the strength of concrete by pulling out a sample section of concrete with pulling devices having a piston pushed by hydraulic or gas pressure. Included in these devices are U.S. Pat. Nos. 3,541,845 to KIERKEGAARDHANSEN, 3,595,072 to RICHARDS, and 3,861,201 to KAINDL.

Still another type of prior art device is a device which performs tensile tests on a sample of material to determine its breaking point, which is then digitally displayed. Examples of this type of device are U.S. Pat. Nos. 3,862,902 to CLAXTON et al., and 4,235,114 to MOHLER.

Yet another type of prior art device is U.S. Pat. No. 2,835,128 to HERRSTRUM. This patent discloses an anchor pull device which measures the strength of a bolt anchor. The patent is concerned with bolt strength and not the strength of the surrounding material in which the bolt is embedded.

All the inventions disclosed in the above mentioned prior art patents appear to have at least some utility as tensile test devices. Most of these prior art patents concern the testing of a small specimen of a substance rather than testing the strength of a substance "in situ." Also, most of these patents relate to arrangements wherein a sample is placed between two jaws of the testing apparatus and one or both of the jaws are pulled away from the sample by any one of several well known power exerting devices, such as, for example, a motor, weights, or a hydraulic powered jack. However, none of the prior art patents disclose a device which could accomplish the purpose which is required of the instant invention. These prior art devices all appear to lack the versatility and complete portability, as well as the accuracy, convenience, and readability of the output, which is provided in the present system.

Therefore, the object of this invention is to provide an insulation test system which will check the strength and bonding of sprayed-on foam insulation on metal cryogenic fuel tanks. Another object is that the system including the power supply be lightweight and completely portable. A further object is that the system provide speed and accuracy without the need for calculations on the part of the operator.

SUMMARY OF THE INVENTION

The present invention is a method and apparatus for testing the tensile strength and bonding strength of sprayed-on foam insulation on metal cryogenic fuel tanks. The device comprises an electro-mechanical pulling device attached to a plug of insulation and a portable, self-contained power supply connected to said pulling device for electrically powering said pulling device. The pulling device is activated to exert pull on the plug until the plug ruptures or pulls loose from the metal. The force necessary to rupture the plug or pull it loose is compared with predetermined acceptable values to ascertain whether the insulation is sufficiently strong and sufficiently well bonded.

The method of testing the tensile strength and bonding strength of sprayed-on foam insulation on metal comprises the steps of: abrading a flat circular area on the surface of said sprayed-on foam insulation; using a circular cutter smaller than the circular area to remove a ring of insulation down to the metal, leaving a test plug of insulation in the center of the circular area; bonding a fitting to the top of the flat test plug; attaching an electro-mechanical pulling device to the top of said fitting; activating said pulling device to exert a pull on the plug sufficient to either pull the plug apart or to debond the plug from the metal; reading the output on the pulling device to determine the applied force which was necessary to pull the plug apart or to debond the insulation; and comparing the indicated applied force with the established acceptable parameters of force to determine whether the strength and bonding of the insuation is within acceptable limits.

BRIEF DESCRIPTION OF THE DRAWINGS

A presently preferred embodiment of the invention will now be described in detail in connection with the accompanying drawings wherein.

DETAILED DESCRIPTION OF THE INVENTION

Figure 1:
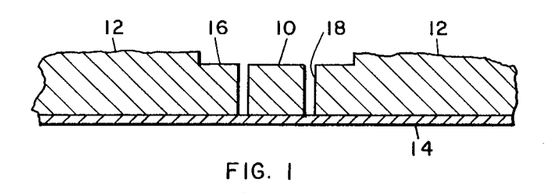
FIG. 1 is a sectional view showing how a test plug is cut in sprayed-on foam insulation attached to metal.

FIG. 1 is a sectional view showing how a test plug 10 is cut in the sprayed-on foam insulation (SOFI) 12 attached to a metal fuel tank 14. First, a circular sander is used to cut a flat circular area 16, preferably about 3 inches in diameter, in the top of the sprayed-on foam insulation 12. This is necessary since the SOFI 12, as sprayed on the metal fuel tank 14, is uneven on top. After the flat area 16 is sanded, a circular cutter (not shown) is used to cut away a ring 18 of foam insulation 12 all the way down to the surface of the metal tank 14 and thereby form a ring slot. Thus, a circular plug 10 of insulation 12, preferably one square inch in cross-sectional area, is isolated from the rest of the insulation 12 covering the fuel tank 14. A circular metal fitting 20 having a flat bottom is then bonded with adhesive to the flat top of the plug 10.

Figure 2:
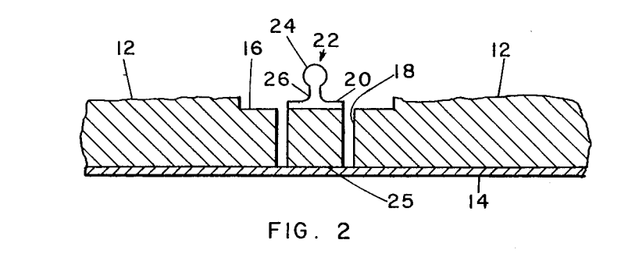
FIG. 2 is a sectional view illustrating how a fitting is bonded to the top of the plug of FIG. 1.

FIG. 2 shows fitting 20 bonded in position on top of plug 10. On the top of fitting 20 is an upstanding projection 22 having a rounded knob 24 on its top with the portion 26 of the projection 22 beneath the knob 24 tapered down so that its cross section is smaller than the cross section of the knob 24.

Figure 3:
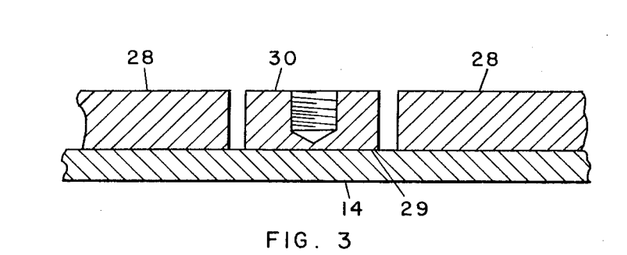
FIG. 3 is a sectional view showing how a test plug is cut in super light ablator insulation attached to metal.

On some areas of the outside of the External Tank (ET) of the Space Shuttle a different type of insulation called Super Light Ablator (SLA) is attached directly to the cryogenic metal fuel tank 14 (see FIG. 3). The SLA insulation 28 is added to the areas of the External Tank where heat is most likely to build up during flight, particularly the front end and the rear dome of the ET. In areas where the SLA insulation 28 is attached to the ET, the SOFI 12 is sprayed over the top of the SLA insulation 28. FIG. 3 shows a layer of SLA 28 attached to the fuel tank 14 but without the usual layer of sprayed-on foam insulation 12 on top of the SLA insulation 28. A plug 30 has been cut in the SLA insulation 28 in a manner similar to the way that plug 10 was cut in FIG. 1. However, since the SLA insulation 28 comes in flat sheets which are bonded to the skin of the fuel tank 14, it is not necessary in this case to first sand a flat circular area before cutting the plug 30.

Figure 4:
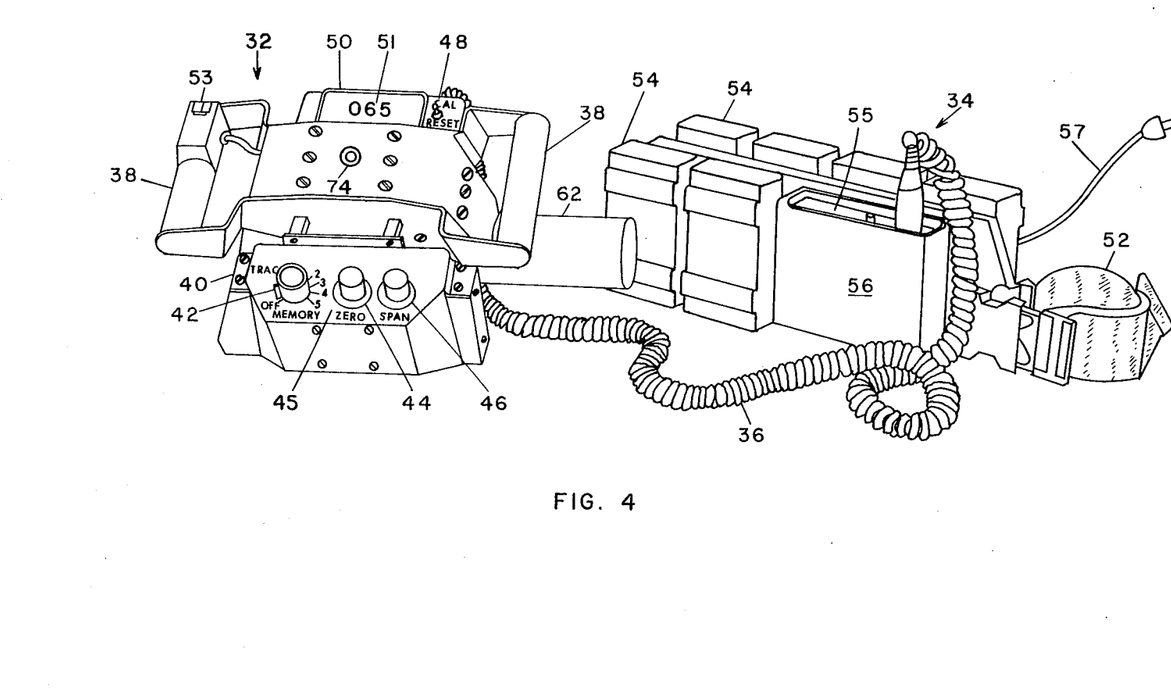
FIG. 4 is a perspective view illustrating the electric motor-powered pulling device and the belt battery pack.

FIG. 4 shows the main portions of the invention, the electric motor-powered pulling device 32 and the belt battery pack 34 connected together by cable 36. The pulling device 32 has two handles 38 attached to its outer case 40, which preferably is made of aluminum. Case 40 is mounted on four legs 41 (FIG. 6) having feet 43. Pulling device 32 weighs about 8.25 pounds and is easily held and operated by one person. Along a side of the pulling device 32 is a control box 45 having upper surface controls for a memory switch 42, a zero rheostat 44, and a span rheostat 46. On the other side is a screen box 50 having a LED digital display 51 of the force required to cause a plug of insulation, either SOFI or SLI, to fail. Associated with the screen box 50 is the calibration reset switch 48. On the left handle 38 is a forward-off-reverse control switch 53 for the motor 60 within case 62. The control box 45 and screen box 50 are part of a known commercial control device of GSE Incorporated of Farmington Hills, MI 48024, known as Model 229-D, Digital Peak Indicator. This control device includes a circuit having a memory which retains the peak force signal provided by the pulling central shaft 74 and displays it on LED display 51.

The belt battery pack 34 is a commercially available item which is integral to the invention but is not considered novel per se. Battery pack 34 is the Anton Bauer Model DB-13, which is manufactured by Anton Bauer Incorporated of Shelton, CT 06484, for use in powering portable television cameras. The unit utilizes a web belt 52 so that it may be worn around the operator's waist. On web belt 52 are mounted six battery boxes 54 and a control box 56. Control box 56 has a panel 55 which contains run-charge switches, battery strength meter, recharging circuit, and a plug for the connecting cable. Recharging cord 57 connects the recharging circuit to a 110V outlet.

Figures 5, 8:
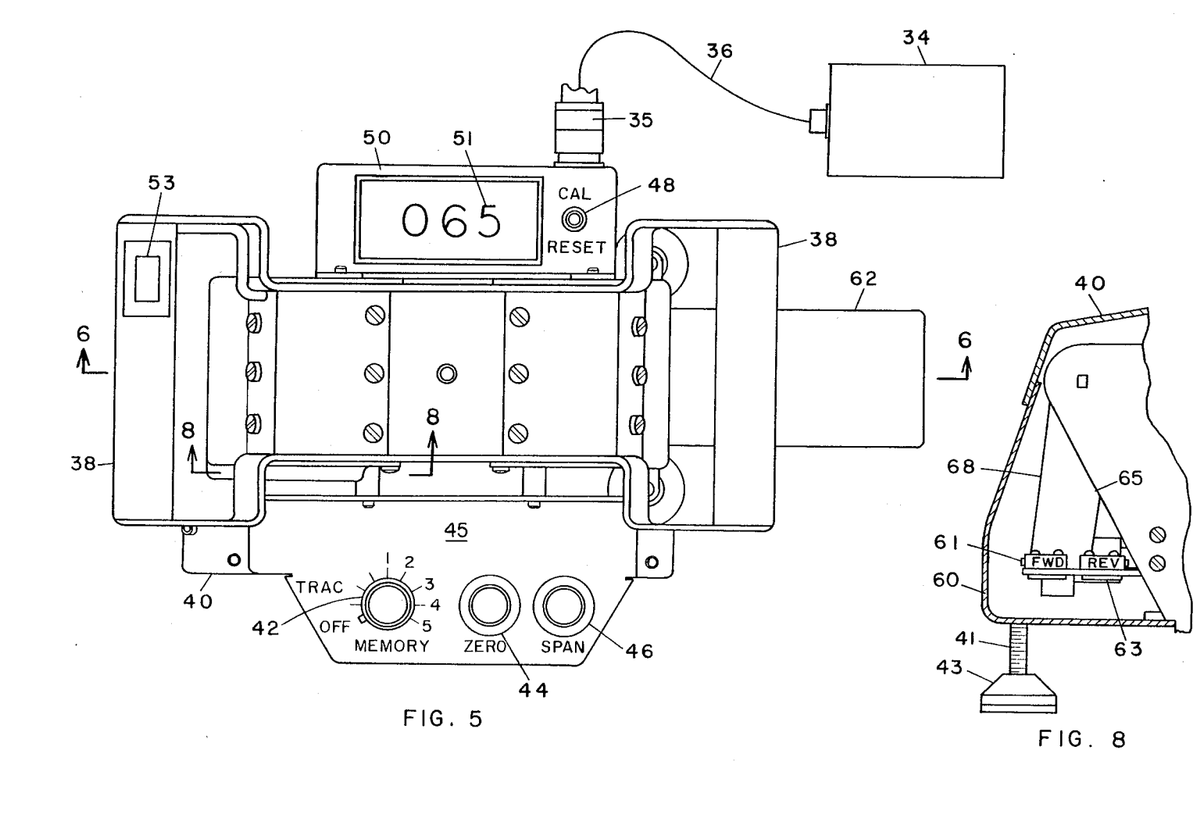
FIG. 5 is a plan view of the case of the pulling device.
FIG. 8 is a sectional view taken along line 8—8 of FIG. 5 showing the limit switch installation of the pulling device.

FIG. 5 shows the details of the top face of the outer case 40 of pulling device 32.

Figure 6:
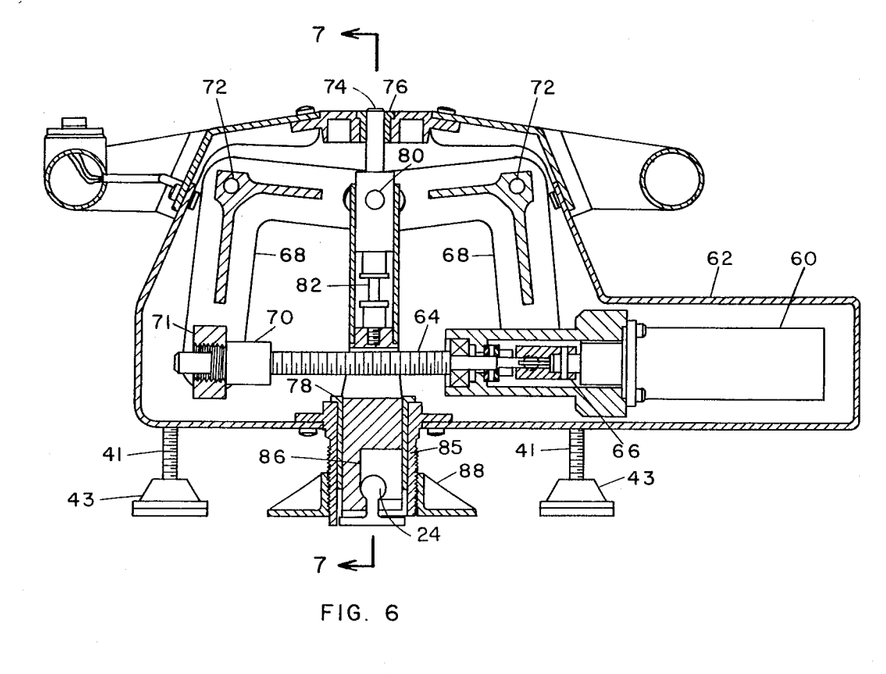
FIG. 6 is a sectional view taken along line 6—6 of FIG. 5 showing the electro-mechanical internal parts of the pulling device.
Figure 7:
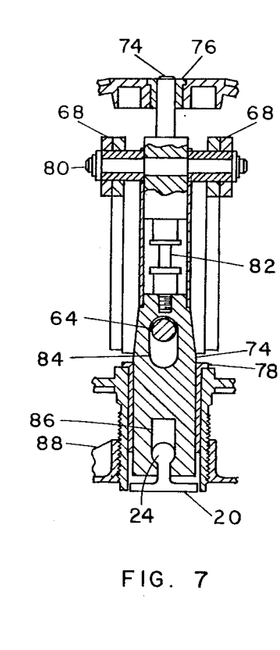
FIG. 7 is a sectional view taken along line 7—7 of FIG. 6 showing the central vertical member of the pulling device.

FIG. 6, which is a sectional view taken along line 6—6 of FIG. 5, shows details of the inner electro-mechanical workings of the pulling device 32. Motor 60 is mounted in a compartment 62 which is an extension of the outer case 40 of the pulling device 32. Motor 60 drives horizontal shaft 64 which is a direct extension of the shaft of motor 60 through coupling 66. Shaft 64 is directly connected to the two bell cranks 68 through ball screws comprising threaded couplings 70 which mesh with nut blocks 71. Thus, as shaft 64 turns in either direction, bell cranks 68 pivot about pivot points 72. The upper ends of bell cranks 68 are attached to the vertical central shaft 74 so that, as the lower ends of bell cranks 68 are pulled inward by motor 60, the upper ends of bell cranks 68 exert an upward pull on central shaft 74. Thus, when the lower end of shaft 74 is attached to fitting 20, which in turn is bonded to plug 10 (see FIG. 2), a pulling force is exerted on plug 10 sufficient to rupture it. The fitting 20 is placed within an off-set hole 86 at the end of the shaft 74 which is also slotted, as shown in FIG. 7, to fit beneath the knob 24 so as to be able to apply a pulling force. As shown in FIG. 8, limit switches 61 and 63 are attached to one of the crank arms for cutting power to the motor 60, when either in the forward or reversed operation mode, by contact of the activation button of the switches 61, 63 with stops positioned to represent the maximum swinging motion of the bell crank arms. The forward stop 60 may be the housing 40 itself and the reverse stop 65 may be the support plate for the bell cranks.

The bottom of the case housing 40 has a cylindrical projection 85 through which the central shaft 74 extends. The lower outer surface of the projection 85 is threaded and has a removable collar 88 threaded thereon which may be turned to contact the surface of the material surrounding the ring slot 18 of FIG. 2. When the central shaft 74 is connected to the fitting 20 secured to the insulation, turning of the collar 88 will cause the housing 40 to raise and place the central shaft 74 in tension.

On occasion, the SOFI 12 will pull loose from the surface of the cyrogenic metal fuel tank 14 at the bond line 25 (FIG. 2) before the plug 10 ruptures. If so, the pulling test indicates whether the bonding withstood the required pulling force of 15 pounds per square inch. If the bonding does not fail, then the test becomes a determination of the strength of the SOFI. The rupture of plug 10 at a pull in excess of 35 pounds per square inch is an indication that the insulation has withstood both the arbitrary bond line strength requirement of 15 pounds per square inch and the arbitrary plug strength requirement of 35 pounds per square inch.

FIG. 7 is a sectional view of the central portion of pulling device 32, taken along line 7—7 of FIG. 5. Details of central shaft 74 are shown. Shaft 74 is held in position by top bushing 76 and bottom bushing 78 and is attached to bell cranks 68 by shaft 80. Load cell 82 together with its strain gauge 83 (FIG. 9) is integral to the central portion of central shaft 74. Horizontal shaft 64 passes through opening 84 of vertical shaft 74 but does not touch the sides of vertical shaft 74.

Figure 9:
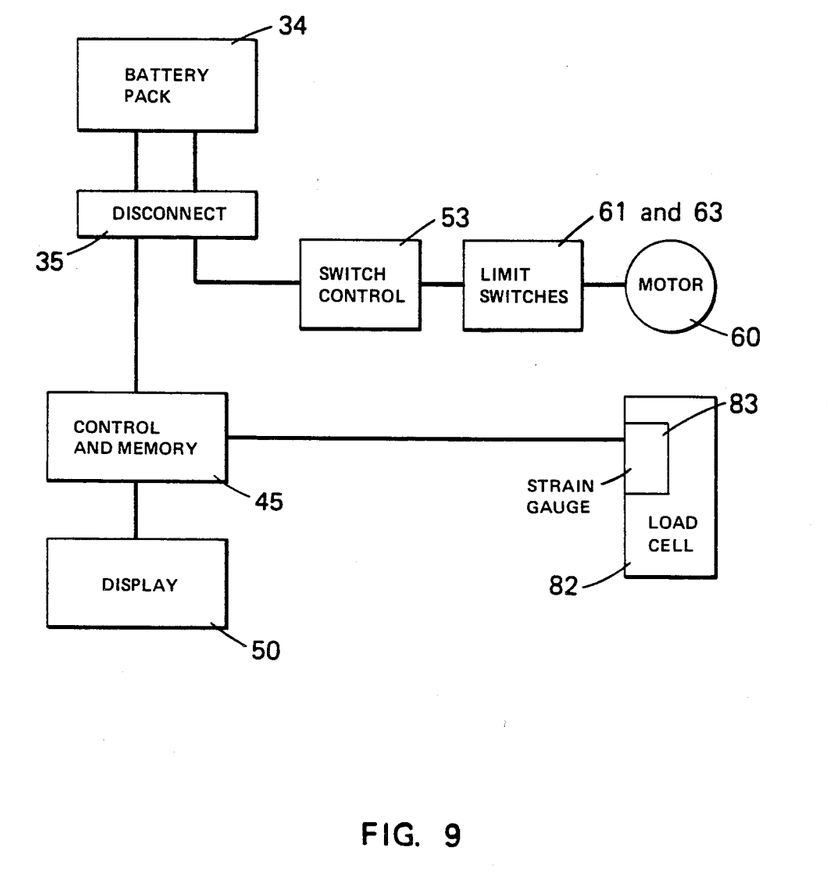
FIG. 9 is a block diagram of the electrical circuit for the pulling device.

As shown in the electrical block diagram of FIG. 9, the battery pack 34 is electrically connected through a disconnect plug 35 mounted on the housing case to the power line of the motor 60 through handle switch control 53 and two limit mechanical activated switches 61 and 63. Also, through the disconnect plug 35 the battery pack 34 is electrically connected to the control and memory box 45 and in turn the display box 50. The strain gauge 83 part of the load cell 82 is electrically connected to the control and memory box 45.

Prior to operation of the invention it is required that the pulling device be calibrated, using features provided for that purpose. In a suitable procedure the battery pack is turned on, and the pulling device 32 is placed on a support so that shaft 32 is not contacting the surface.

The cal/reset switch 48 is then set to "cal" and the span rheostat 46 is rotated until the desired calibration value for load cell 82 appears on the display 51. The switch 48 is then moved to "reset", and zero rheostat 44 is rotated until zero shows on display 51. These steps are repeated until the calibration value and zero repeat without further adjustment of the rheostats.

In operation of the invention the pulling device 32 is connected to plug 10 by inserting test plug knob 24 into offset hole 86 at the end of plug pulling shaft 74 and centering the plug with the shaft. Initial tension is provided by turning collar 88 until it contacts the surface of insulation 12. Memory switch 42 is then set to correspond to the particular track being used. The forward switch 53 is depressed and tensile load is applied. Tensile load is increased until failure of either the insulation 12 or the insulation bond line 25. The forward switch 53 is then returned to "off" and the failure load is recorded. After determination of the failure load on the first test plug 10 is completed, the track switch 42 may be turned to the next track and another plug 10 tested. Five tracks are provided, thus allowing five plugs 10 to be tested prior to manually recording the test values. The test values will appear on the digital readout 51 when the track switch 42 is set to each track. After the test values are recorded, the tracks are reset to zero before any additional testing.

After each plug 10 is tested, the shaft 74 may require moving to a lower position so connection to the test plug 10 can be made. The shaft 74 can be lowered by depressing the forward-off-reverse switch 53 in the reverse position. Forward and reverse limit switches 61 and 63 as discussed before are provided to prevent overextension of the shaft 74. The tensile force is provided by the bell cranks 68 which are powered by the electric motor 60 and ball screw comprising threaded shaft 70 and nut blocks 71. The tensile force is measured by the load cell 82 integral to the shaft 74 and is read out on LED display 51.

The present invention represents a considerable improvement over the prior art system described above. In addition to the advantages of portability, speed, and accuracy which the present invention has shown over the Porta Pull system, the present system does not have the disadvantage of possibly damaging the insulation beyond repair. With Porta Pull, at the moment the rupture occurs, the device bounces away from the surface of the insulation. The weight of the device with its heavy cylinder and piston causes it to fall back down against the insulation with considerable force. Thus, a potential danger of irreparable damage to both the insulation and the tank wall is eliminated by the use of the present invention.

The present invention has been specifically described for purposes of illustration as being used in testing portions of the insulation on the exterior walls of the External Tank of the Space Shuttle, the walls consisting of curved metal plates having a form composite sprayed on them. However, it is obvious that the invention also finds utility in the testing of insulation attached to panels composed of a wide variety of other kinds of materials.

The nature and scope of the present invention having been indicated and the preferred embodiment of the invention having been specifically described, what is claimed is:

1. Apparatus for determining tensile and bond strength of materials comprising:

a housing;
a load shaft positioned by said housing for longitudinal movement, said load shaft adapted to be attached at one end of the material to be tested;
a motor and mechanical means for longitudinally moving said load shaft; and
a portable, self-contained power supply for providing power to said motor and display means;
said housing having a display means for indicating stress experienced by said load shaft when pulling on the material to be tested;
said load shaft having means for providing a signal to said display means of the stress caused by its pulling on the test material.

2. Apparatus as set forth in claim 1 further comprising:
handle means on said housing enabling a person to hold and operate the apparatus; and
feet means for supporting said housing on the material to be tested.

3. Apparatus as set forth in claim 1 wherein:
said load shaft means for providing a signal to said display means is a load cell which produces an electrical signal corresponding to the pulling stress experienced by said load shaft; and including
a control means receiving said electrical signal from said load cell and providing a digital signal to said display means.

4. Apparatus as set forth in claim 3 wherein:
said control means include a memory means for holding the signal representing the maximum pulling stress experienced by the load shaft and providing said signal to said display means following failure of the material to be tested.

5. Apparatus as set forth in claim 1 wherein:
said motor and mechanical means having a pair of bell crank lever on opposite sides of said load shaft;
each bell crank lever pivotally supported by said housing at the juncture of the two arms of the bell crank lever and pivotally secured at the end of one lever arm to said load shaft and pivotally secured at the end of the other lever arm to a common rotatable shaft;
said common rotatable shaft secured to the shaft of a motor whereby said motor shaft depending on direction of rotation may cause the bell crank lever arms pivotally joined to said common shaft to pull inward or outward together and cause the other bell crank lever arms to pivot upwardly or downwardly together and pull the load shaft upwardly or downwardly.

6. Apparatus as set forth in claim 5 wherein:
limit switches are attached to an arm of said bell crank levers for stopping said motor when the pivoting movement of the bell crank levers exceed certain limits so as to prevent damages to the apparatus.

7. Apparatus as set forth in claim 1 further comprising:
the end of said load shaft adapted to be attached to the material to be tested having a slotted offset hole and a removable fitting with a knob therein fitted within said hole and supported by the surrounding structure forming the slot, said fitting adapted to be bonded to the surface of the material to be tested.

8. A pulling apparatus comprising:
a housing;
a vertical elongated shaft positioned by said housing for longitudinal movement from an upper position to a lower position;
attachment means at the lower end of said shaft for attachment to an object to be pulled;
a motor means having a horizontal threaded shaft;
a pair of bell crank levers on opposite sides of said vertical shaft;
each bell crank lever pivotally supported by said housing at the juncture of the two arms of the bell crank lever, and pivotally secured at the end of one lever arm to a separate block threaded onto said horizontal threaded shaft and pivotally secured at the end of the other lever arm to said vertical shaft whereby said motor threaded shaft depending on direction of rotation may cause the bell crank lever arms pivotally joined to blocks threaded on said motor threaded shaft to pull either toward or away from each other causing the other bell crank lever arms to pivot upwardly or downwardly together and thereby pull or push the vertical shaft upwardly or downwardly.

9. A pulling apparatus as set forth in claim 8 further comprising:
a display means for indicating the stress experience by said vertical shaft when pulling on the material to be tested,
said vertical shaft having means for providing a signal to said display means of the pulling stress placed upon said vertical shaft.

10. A pulling apparatus as set forth in claim 9 wherein:
said vertical shaft means for providing a signal of the pulling stress is a load cell which produces an electrical signal corresponding to the pulling stress; and including,
a control means receiving said electrical signal from said load cell and providing a signal to said display means.

11. A pulling apparatus as set forth in claim 10 further comprising:
an electrical power supply means for providing necessary electrical power.

12. A pulling apparatus as set forth in claim 11 further comprising:
a pair of handles on said housing enabling a person to hold and operate the apparatus; and
feet means for supporting said housing on a surface.

13. A pulling apparatus as set forth in claim 12 wherein:
the lower end of said vertical shaft is slotted with an off-set hole; and including,
a removable fitting with an upper knob thereon fitted within said hole and supported by the surrounding structure forming the slot, said fitting adapted to be secured to the surface of material to be pulled by said vertical shaft.

14. A method of testing the tensile strength and bonding strength of sprayed-on foam insulation bonded to another material comprising:
abrading a flat circular area on the surface of said sprayed-on foam insulation;
using a circular cutter smaller than the circular area to remove a ring of insulation down to the other material, leaving a test plug of insulation in the center of the circular area;
bonding a fitting to the top of the flat test plug;

attaching an electro-mechanical pulling device having a force indicator to the top of said fitting;
activating said pulling device to exert a pull on the plug sufficient to either pull the plug apart or to debond the plug from the other material;
reading the indicated force output on the pulling device to determine the applied force which was necessary to pull the plug apart or to debond the insulation.

15. A method according to claim 14 including:
comparing the applied force output with the establish parameters of force to determine whether the strength and bonding of the material is within acceptable limits.

* * * * *